United States Patent
Dahlke et al.

(10) Patent No.: US 10,093,761 B2
(45) Date of Patent: Oct. 9, 2018

(54) FLUORINE-CONTAINING POLYMER COMPRISING A SULFINATE-CONTAINING MOLECULE

(75) Inventors: Gregg D. Dahlke, St. Paul, MN (US); Denis Duchesne, Woodbury, MN (US); Tatsuo Fukushi, Woodbury, MN (US); Werner M. Grootaert, Oakdale, MN (US); Miguel A. Guerra, Woodbury, MN (US); Harald Kaspar, Burgkirchen (DE); Larry A. Last, Moulton, AL (US); Peter J. Scott, Madison, AL (US); Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 260 days.

(21) Appl. No.: 13/992,493

(22) PCT Filed: Dec. 16, 2011

(86) PCT No.: PCT/US2011/065339
§ 371 (c)(1),
(2), (4) Date: Jun. 7, 2013

(87) PCT Pub. No.: WO2012/083107
PCT Pub. Date: Jun. 21, 2012

(65) Prior Publication Data
US 2013/0251930 A1 Sep. 26, 2013

Related U.S. Application Data

(60) Provisional application No. 61/424,109, filed on Dec. 17, 2010.

(51) Int. Cl.
| | |
|---|---|
| *C08F 228/02* | (2006.01) |
| *C07C 17/275* | (2006.01) |
| *C07C 303/22* | (2006.01) |
| *C07C 313/04* | (2006.01) |
| *C08F 214/18* | (2006.01) |

(52) U.S. Cl.
CPC .......... *C08F 228/02* (2013.01); *C07C 17/275* (2013.01); *C07C 303/22* (2013.01); *C07C 313/04* (2013.01); *C08F 214/18* (2013.01); *C08F 214/182* (2013.01); *Y10T 428/139* (2015.01)

(58) Field of Classification Search
CPC ... C07C 313/02; C07C 313/04; C07C 17/275; Y10T 428/139; Y10T 428/182; C08L 27/12; C08L 27/16; C08F 214/182; C08F 214/08; C08F 214/184; C08F 214/186; C08F 214/20; C08F 214/202; C08F 214/205; C08F 214/207; C08F 214/22; C08F 214/222; C08F 214/225; C08F 214/227; C08F 214/24; C08F 214/242; C08F 214/245; C08F 214/247; C08F 214/262; C08F 214/265; C08F 214/267; C08F 214/28; C08F 214/282; C08F 214/285; C08F 214/287
USPC ....... 526/243; 525/200; 521/27, 36; 562/125
See application file for complete search history.

(56) References Cited

U.S. PATENT DOCUMENTS

| | | | | |
|---|---|---|---|---|
| 4,332,665 A | * | 6/1982 | Kimoto et al. | ............... 204/296 |
| 4,544,458 A | | 10/1985 | Grot | |
| 4,626,553 A | * | 12/1986 | Hane et al. | ..................... 521/27 |
| 5,285,002 A | | 2/1994 | Grootaert | |
| 5,378,782 A | | 1/1995 | Grootaert | |
| 5,585,449 A | | 12/1996 | Arcella | |
| 6,002,055 A | | 12/1999 | Yang | |

(Continued)

FOREIGN PATENT DOCUMENTS

| | | |
|---|---|---|
| CN | 1337786 | 2/2002 |
| CN | 101 721 922 | 6/2010 |

(Continued)

OTHER PUBLICATIONS

Chanda, Manas, and Salil K. Roy. Plastics Technology Handbook, Boca Raton, FL:CRC/Taylor & Francis Group, 2007, ISBN 0-8493-7039-6.*

(Continued)

*Primary Examiner* — Lee E Sanderson
(74) *Attorney, Agent, or Firm* — Julie Lapos-Kuchar

(57) ABSTRACT

Described herein is a composition having a fluoropolymer derived from the polymerization of a monomer and a sulfinate-containing molecule, wherein the sulfinate-containing molecule is selected from the group consisting of Formula (I), Formula (II); and combinations thereof, wherein $X_1$, $X_2$, and $X_3$ are each independently selected from H, F, Cl, a $C_1$ to $C_4$ alkyl group, and a $C_1$ to $C_4$ fluorinated alkyl group; R is a linking group; $Z_1$ and $Z_2$ are independently selected from F, $CF_3$, and a perfluoroalkyl group; $R_1$ and $R_2$ are end-groups; p is 0 or 1; m is at least 1; and M is a cation. Also disclosed are methods of making and articles thereof.

Formula (I)

(a) $CX_1X_3 = CX_2 - (R)_p - CZ_1Z_2 - SO_2M$      (a)

Formula (II)

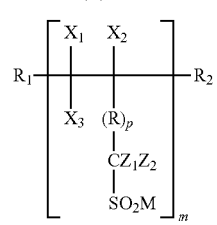

13 Claims, No Drawings

(56) References Cited

U.S. PATENT DOCUMENTS

| | | | |
|---|---|---|---|
| 6,462,228 B1* | 10/2002 | Dams | 562/125 |
| 6,624,328 B1 | 9/2003 | Guerra | |
| 7,375,157 B2 | 5/2008 | Amos | |
| 7,754,795 B2 | 7/2010 | Hintzer | |
| 2004/0039142 A1 | 2/2004 | Yang | |
| 2004/0192868 A1* | 9/2004 | Kaspar et al. | 526/249 |
| 2004/0213936 A1* | 10/2004 | Yoshimoto | A61L 29/041 428/36.91 |
| 2005/0187363 A1* | 8/2005 | Oharu | C08F 214/26 526/247 |
| 2006/0052557 A1* | 3/2006 | Kaspar | C08F 214/18 526/242 |
| 2007/0015937 A1 | 1/2007 | Hintzer | |
| 2009/0124755 A1 | 5/2009 | Coughlin | |
| 2009/0258958 A1* | 10/2009 | Ford | A61L 27/16 521/56 |
| 2009/0312517 A1 | 12/2009 | Yang et al. | |

FOREIGN PATENT DOCUMENTS

| | | |
|---|---|---|
| CN | 102 008 905 | 4/2011 |
| CN | 102633688 | 8/2012 |
| EP | 0 289 869 | 11/1988 |
| JP | 57 128703 | 8/1982 |
| JP | 2 213488 | 8/1990 |
| JP | 6 032918 | 2/1994 |
| JP | 2006/131588 | 5/2006 |
| WO | WO 1997/02300 | 1/1997 |
| WO | WO 2011/156936 | 12/2011 |
| WO | WO 2012/082454 | 6/2012 |
| WO | WO 2012/082546 | 6/2012 |
| WO | WO 2012/082551 | 6/2012 |
| WO | WO 2012/082695 | 6/2012 |
| WO | WO 2012/082703 | 6/2012 |
| WO | WO 2012/166578 | 12/2012 |

OTHER PUBLICATIONS

Auhl, "Molecular Characterization of Semi-Fluorinated Copolymers with a Controlled Amount of Long-Chain Branching", Macromolecules, 2006, vol. 39, No. 6, pp. 2316-2324.

International Search Report for PCT International Application No. PCT/US2011/065339, dated Jun. 19, 2012, 4 pages.

Shroff, "Assessment of NMR and Rheology for the Characterization of LCB in Essentially Linear Polyethylenes", Macromolecules, 2001, vol. 34, pp. 7362-7367.

Shroff, "Long-Chain-Braching Index for Essentially Linear Polyethylenes", Macromolecules, 1999 vol. 32, pp. 8454-8464.

Stange, "Linear Rheological Properties of the Semifluorinated Copolymer Tetrafluoroethylene-Hexafluoropropylene-Vinylindenfluoride (THV) with Controlled Amounts of Long-Chain Branching", Macromolecules, 2007, vol. 40, No. 7, pp. 2409-2416.

* cited by examiner

FLUORINE-CONTAINING POLYMER COMPRISING A SULFINATE-CONTAINING MOLECULE

CROSS REFERENCE TO RELATED APPLICATIONS

This application claims priority to U.S. provisional Application No. 61/424,109, filed Dec. 17, 2010, the disclosure of which is incorporated by reference in its entirety herein.

TECHNICAL FIELD

The present disclosure relates to a composition that comprises a fluorine-containing polymer derived from the polymerization of a monomer and a sulfinate-containing molecule.

BACKGROUND

Fluorine-containing polymers have been long known and have been used in a variety of applications because of several desirable properties such as heat resistance, chemical resistance, weatherability, UV-stability, etc.

Further, it is known that branching in polymers can result in desirable properties. For example, these polymers can have favorable rheological properties relative to their linear counterparts.

Bifunctional comonomer and halogenated comonomers have been used to cause branching of a fluoropolymer during polymerization. For example, U.S. Pat. No. 5,585,449 (Arcella, et al.) discloses the use of bisolefins to achieve long chain branching, while U.S. Pat. No. 7,375,157 (Amos et al.) discloses the use of halogenated olefins to cause branching of a fluoropolymer during polymerization.

SUMMARY

There is a need for new fluorine-containing polymers constructions and/or alternative processes for making branched polymers.

In one aspect, a composition is described comprising: a fluorine-containing polymer derived from the polymerization of a monomer and a sulfinate-containing molecule, wherein the sulfinate-containing molecule is selected from the group consisting of:

Formula (I)

(a)

$$CX_1X_3\!=\!\!CX_2\!-\!(R)_p\!-\!CZ_1Z_2\!-\!SO_2M$$

Formula (II)

(b)

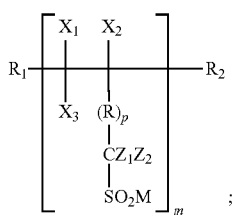

and
(c) combinations thereof,
wherein $X_1$, $X_2$, and $X_3$ are each independently selected from H, F, Cl, a $C_1$ to $C_4$ alkyl group, and a $C_1$ to $C_4$ fluorinated alkyl group; R is a linking group; $Z_1$ and $Z_2$ are independently selected from F, $CF_3$, and a perfluoroalkyl group; $R_1$ and $R_2$ are end-groups; p is 0 or 1; m is at least 2; and M is a cation.

In another aspect, polymer comprising an end-group is described having a structures from group consisting of:

Formula (III)

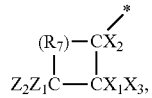

Formula (IV)

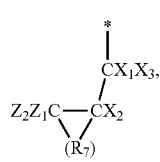

and combinations thereof;
wherein $X_1$, $X_2$, and $X_3$ are each independently selected from H, F, Cl, a $C_1$ to $C_4$ alkyl group, and a $C_1$ to $C_4$ fluorinated alkyl group; $R_7$ is a linking group comprising at least 2 or more catenary atoms; and $Z_1$ and $Z_2$ are independently selected from F, $CF_3$, and a perfluoroalkyl group.

In yet another aspect, an article is described comprising the composition described above.

In still another aspect, a method of making is described comprising: (i) providing a monomer and a sulfinate-containing molecule, wherein the sulfinate-containing molecule is selected from the group consisting of Formula (I)

(a)

$$CX_1X_3\!=\!\!CX_2\!-\!(R)_p\!-\!CZ_1Z_2\!-\!SO_2M$$

Formula (II)

(b)

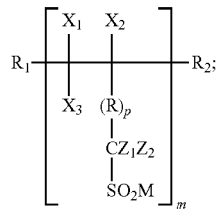

and
(c) combinations thereof,
wherein $X_1$, $X_2$, and $X_3$ are each independently selected from H, F, Cl, a $C_1$ to $C_4$ alkyl group, and a $C_1$ to $C_4$ fluorinated alkyl group; R is a linking group; $Z_1$ and $Z_2$ are independently selected from F, $CF_3$, and a perfluoroalkyl group; $R_1$ and $R_2$ are end-groups; p is 0 or 1; m is at least 2; and M is a cation; and (ii) polymerizing the monomer in the presence of the sulfinate-containing molecule.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more.

"and/or" is used to indicate one or both stated cases may occur, for example A and/or B includes, (A and B) and (A or B).

"Oligomer" means less than 20,000 g/mol, less than 15,000 g/mol, less than 10,000 g/mol, less than 5,000 g/mol, less than 2,000 g/mol, less than 1,000 g/mol, and even less than 500 g/mol.

"Linking group" means a divalent linking group. In one embodiment, the linking group includes at least 1 carbon atom (in some embodiments, at least 2, 4, 8, 10, or even 20 carbon atoms). The linking group can be a linear or branched, cyclic or acyclic structure, that may be saturated or unsaturated, substituted or unsubstituted, and optionally contains one or more hetero-atoms selected from the group consisting of sulfur, oxygen, and nitrogen, and/or optionally contains one or more functional groups selected from the group consisting of ester, amide, sulfonamide, carbonyl, carbonate, urethane, urea, and carbamate. In another embodiment, the linking group does not comprise a carbon atom and is a catenary heteroatom such as oxygen, sulfur, or nitrogen.

"Sulfinate" is used to indicate both sulfinic acids and sulfinic acid salts.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Recently, unique monomers and oligomers comprising pendent sulfinic acids and salts thereof have been discovered. See U.S. Prov. Appl. Nos. 61/492,885, 61/424,138, 61/424,109, 61/424,107, 61/424,146, and 61/424,153, all herein incorporated by reference, and all filed on 17 Dec. 2011. The present disclosure is directed toward a composition comprising a fluorine-containing polymer derived from the polymerization of a monomer and a sulfinate-containing molecule.

The sulfinate-containing molecule of the present disclosure is selected from the group consisting of:

Formula (I)

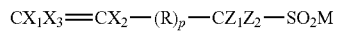

Formula (II)

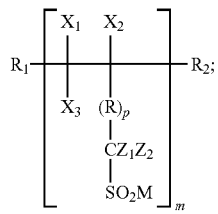

and (c) combinations thereof, wherein $X_1$, $X_2$, and $X_3$ are each independently selected from H, F, Cl, a $C_1$ to $C_4$ alkyl group, and a $C_1$ to $C_4$ fluorinated alkyl group; R is a linking group; $Z_1$ and $Z_2$ are independently selected from F, $CF_3$, and a perfluoroalkyl group; $R_1$ and $R_2$ are end-groups; p is 0 or 1; m is at least 2; and M is a cation.

In one embodiment R may be non-fluorinated, partially fluorinated, or perfluorinated. In some embodiments, the hydrogen atom in R may be replaced with a halogen other than fluorine, such as a chlorine. R may or may not comprise double bonds. R may be substituted or unsubstituted, linear or branched, cyclic or acyclic, and may optionally comprise a functional group (e.g., esters, ethers, ketones, amines, halides, etc.). In one embodiment, R is a catenary heteroatom such as oxygen, sulfur, or nitrogen.

$R_1$ and $R_2$ are end-groups generated during oligomerization. These end-groups are independently selected from hydrogen, iodine, bromine, chlorine, a linear or branched alkyl, and a linear or branched fluoroalkyl group, optionally containing catenary heteroatoms. In some embodiments, the alkyl or fluoroalkyl group has up to 20 carbon atoms. These end-groups are determined based on the initiator or chain transfer agent used and the reaction conditions used to form the oligomer. For example, when a nonfluorinated initiator is used, hydrogen atoms may be present as $R_1$ and $R_2$ in Formula (II). In one embodiment, $R_1$ and $R_2$ are perfluorinated such as when a perfluorinated initiator is used.

As used herein M represents a cation. Exemplary cations useful in the present disclosure include $H^+$, $NH_4^+$, $PH_4^+$, $H_3O^+$, $Na^+$, $Li^+$, $Cs^+$, $Ca^{+2}$, $K^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and combinations thereof.

Formula (II) as disclosed herein is an oligomer, meaning that Formula (II) has a number average molecular weight of no more than 20,000 grams/mole, 15,000 grams/mole, 10,000 grams/mole, 5,000 grams/mole, 2,000 grams/mole, 1000 grams/mol, or even 500 grams/mole. In one embodiment, m is at least 1, 2, 3, 4, 6, 8, 10, or even at least 15.

In one embodiment, the sulfinate-containing molecule of Formula (I), R is selected from: —$(CH_2)_a$—, —$(CF_2)_a$—, —O—$(CF_2)_a$—, —$(CF_2)_a$—O—$(CF_2)_b$—, —O$(CF_2)$—O—$(CF_2)_b$—, —$(CF_2)_a$—[O—$(CF_2)_b]_c$—, —O$(CF_2)_a$—[O—$(CF_2)_b]_c$—, —[$(CF_2)_a$—O]$_b$—[$(CF_2)_c$—O]$_d$—, —O[$(CF_2)_a$—O]$_b$—[$(CF_2)_c$—O]$_d$—, —O—[$CF_2CF(CF_3)$O]$_a$—$(CF_2)_b$—, and combinations thereof, wherein a, b, c, and d are independently at least 1, 2, 3, 4, 10, 20, etc.

In one embodiment, the sulfinate-containing molecule of Formula (I) is selected from the group consisting of: $CF_2$=CF—O$(CF_2)_n$—$SO_2M$; $CF_2$=CF—O[$CF_2CF(CF_3)$O]$_n$$(CF_2)_o$—$SO_2M$; $CH_2$=CH—$(CF_2)_n$—$SO_2M$; and combinations thereof, where n is at least 1, o is at least 1, and M is a cation.

In one embodiment, the sulfinate-containing molecule of Formula (II) comprises a segment selected from the group consisting of:

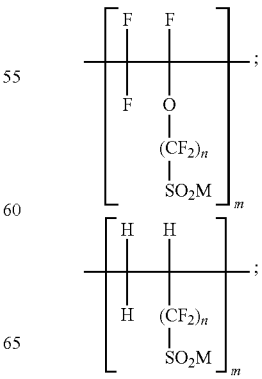

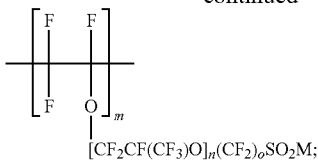

$[CF_2CF(CF_3)O]_n(CF_2)_oSO_2M;$ and combinations thereof, where n is at least 1; m is at least 1; o is at least 1, and M is a cation.

The oligomers and monomers of the present disclosure can be made using methods as disclosed in U.S. Prov. Appl. Nos. 61/492,885, 61/424,138, 61/424,109, 61/424,107, 61/424,146, and 61/424,153.

In the present disclosure, a fluorine-containing polymer is derived from the polymerization of a monomer and a sulfinate-containing molecule. The monomer can be selected from non-fluorinated, partially fluorinated, and fully fluorinated monomers.

In one embodiment, the monomer is selected from: dienes (including nonfluorianted, partially fluorinated and perfluorinated dienes, for example $CH_2=CHR_fCH=CH_2$, wherein Rf is a perfluorinated alkylene group, which may comprise 2, 3, 4, 5, 6, 7, 8, 9, 10, 11, 12 carbon atoms for example), halogenated alkenes, a fluoroalkyl substituted ethylene, allyl iodide, fluorinated alkyl vinyl ethers, fluorinated alkoxy vinyl ethers, olefins, acrylates, styrene, vinyl ethers, and combinations thereof.

Exemplary monomers include: tetrafluoroethylene, hexafluoropropylene, trifluoroethylene, vinylidene fluoride, vinyl fluoride, bromotrifluoroethylene, chlorotrifluoroethylene, $CF_3CH=CF_2$, $C_4F_9CH=CH_2$, $CF_2=CHBr$, $CH_2=CHCH_2Br$, $CF_2=CFCF_2Br$, $CH_2=CHCF_2CF_2Br$, $CH_2=CHI$, $CF_2=CHI$, $CF_2=CFI$, $CH_2=CHCH_2I$, $CF_2=CFCF_2I$, $CH_2=CHCF_2CF_2I$, $CF_2=CFCH_2CH_2I$, $CF_2=CFCF_2CF_2I$, $CH_2=CH(CF_2)_6CH_2CH_2I$, $CF_2=CFOCF_2CF_2I$, $CF_2=CFOCF_2CF_2CF_2I$, $CF_2=CFOCF_2CF_2CH_2I$, $CF_2=CFCF_2OCH_2CH_2I$, CF2=CFO(CF2)3-OCF2 CF2, CH2=CHBr and others as is known in the art.

In the present disclosure, the oligomers or monomers comprising the sulfinic acid or salt thereof, may be used in polymerization reactions of polymers. Although not wanting to be bound by theory, it is believed that the fluorinated sulfinate anion ($RfSO_2^-$), acting as an electron donor to form a fluorinated radical (Rf) by a single electron transfer (SET) to an oxidizing agent or electron acceptor to generate $Rf-SO_2$. following $SO_2$-elimination. Thus, the sulfinated compounds may act as an initiator in radical polymerization reactions and theoretically be consumed and incorporated into the polymer chain during the polymerization. Although not wanting to be bound by theory, it is also believed that because of the fast SET reaction of the fluorinated sulfinate anion with a strong oxidizing agent or a strong electron acceptor, such as $(NH_4)_2S_2O_8$ to form a fluorinated radical, polymers made using these initiator compounds may have reduced or no polar end-groups generated from the oxidizing agent, which may aid in stability of the resulting polymer. The application of the combined fluorinated sulfinate with an oxidation agent as co-initiator has been demonstrated, such as in U.S. Pat. No. 5,285,002 (Grootaert).

The sulfinate-containing molecules as disclosed herein may also impart branching of the polymer during polymerization. In one embodiment, the sulfinate-containing molecule of Formula (I) comprises both a double bond and a sulfinate functional group, both of which can react under free radical polymerization, the vinyl group acting as any traditional vinyl group would react and the sulfinate group as described above. In another embodiment, the sulfinate-containing molecule (e.g., an oligomer) of Formula (II) comprises multiple sulfinate residues, each of which is capable of forming a branch chain after generating the radical species.

The level of branching or non-linearity can be characterized through the long chain branching index (LCBI). The LCBI can be determined as described in R. N. Shroff, H. Mavridis; Macromol., 32, 8464-8464 (1999) & 34, 7362-7367 (2001) according to the equation:

$$LCBI = \frac{\eta_{0,br.}^{1/a}}{[\eta]_{br.}} \cdot \frac{1}{k^{1/a}} - 1 \qquad \text{eq. 1}$$

In the above equation, $\eta_{0,br}$ is the zero shear viscosity (units Pa's) of the branched polymer measured at a temperature T and $[\eta]_{br}$ is the intrinsic viscosity (units ml/g) of the branched polymer at a temperature T' in a solvent in which the branched polymer can be dissolved and a and k are constants. These constants are determined from the following equation:

$$\eta_{0,lin} = k \cdot [\eta]_{lin}^a. \qquad \text{eq. 2}$$

wherein $\eta_{0,lin}$ and $[\eta]_{lin}$ represent respectively the zero shear viscosity and intrinsic viscosity of the corresponding linear polymer measured at the respective same temperatures T and T' and in the same solvent. Thus, the LCBI is independent of the selection of the measurement temperatures and solvent chosen provided of course that the same solvent and temperatures are used in equations 1 and 2. The zero shear viscosity and intrinsic viscosity are typically determined on freeze coagulated polymers.

The values a and k along with the test conditions for some fluoropolymers are listed in the following table:

| Polymer | test condition | a-value | k-value |
|---|---|---|---|
| $TFE_{39}/HFP_{11}/VDF_{50}$ | A | 5.8 | $2.4 \cdot 10^{-8}$ |
| $TFE_{24.5}/HFP_{23}/VDF_{52.5}$ | A | 5.8 | $5.5 \cdot 10^{-8}$ |
| $VDF_{78}/HFP_{22}$ | A | 5.8 | $1.5 \cdot 10^{-8}$ |
| polyvinylidene fluoride | B | 5.8 | $1.2 \cdot 10^{-8}$ |
| polyvinylidene fluoride | C | 5.8 | $2.2 \cdot 10^{-8}$ |

In the above table, the indexes to the monomer units in the polymer indicate the amount of the respective unit in mole % and the test conditions are as follows:

A: shear viscosity at 265° C. and the intrinsic viscosity in methyl ethyl ketone at 35° C.

B: shear viscosity at 230° C. and the intrinsic viscosity in dimethylformamide at 23° C.

C: shear viscosity at 230° C. and the intrinsic viscosity in dimethylformamide at 110° C.

It can be observed from the above table that the constant a-values appear to be independent of the polymer tested whereas the k-value varies with composition of the polymer and test condition used.

The LCBI of the polymer used should have a value of at least 0.2. Generally, the effectiveness of the polymer to decrease melt defects will increase with increasing value of the LCBI for polymers having similar zero shear rate viscosities ($\eta_0$). However, when the level of branching (and thus the LCBI value) becomes too large, the polymer may have a gel fraction that cannot be dissolved in an organic solvent. One skilled in the art through routine experimentation may readily determine the appropriate value of LCBI. Generally, the LCBI will be between 0.2 and 5, preferably between 0.5 and 1.5. In one embodiment, the LCBI is greater than 0.2, 0.5, 1, 1.5, 2, 2.5, 4, or even 6.

In one embodiment of the present disclosure, the compositions of the present disclosure comprise a higher LCBI value, than the same polymer prepared with an alternate branching agent, such as a halogenated olefin.

The atoms of $X_1$, $X_2$, and $X_3$ and the selection of the monomer will determine the fluorination (i.e., perfluorinated, partially fluorinated, or non-fluorinated) of the polymer. In one embodiment, the polymers of the present disclosure are perfluorinated. In other words, all of the C—H bonds in the polymer backbone are replaced by C—F bonds, although the end groups may or may not be fluorinated. In one embodiment, the polymers of the present disclosure are highly fluorinated, meaning that 80%, 90%, 95%, or even 99% of the C—H bonds in the polymer backbone are replaced by C—F bonds. In another embodiment, the polymers of the present disclosure are partially fluorinated, meaning the polymer backbone (excluding the end groups) comprises at least one C—H bond and one C—F bond. In another embodiment, the polymers of the present disclosure are non-fluorinated, meaning that the polymer does not comprise any C—F bonds in the polymer backbone, however, the endgroups may or may not be fluorinated.

The resulting polymers of the present disclosure may be amorphous, i.e. they have no melting point or hardly show a melting point; semicrystalline, i.e. polymers that have a clearly detectable melting point; or even crystalline.

The sulfinate-containing molecules should generally be used at fairly low levels to avoid extensive branching during the polymerization. The amount of sulfinate-containing molecules that is typically used in the polymerization to cause a desired amount of branching of the fluoropolymer depends on the nature of the modifier used and on the polymerization conditions such as e.g. reaction time, temperature, and timing of the addition of the sulfinate-containing molecule. The amount of sulfinate-containing molecule to be used is selected such that the desired LCBI value is attained. The optimal amount of sulfinate-containing molecules can be readily determined by one skilled in the art but is generally not more than 1% by weight and for example not more than 0.7% or 0.5% by weight based on the total weight of monomers fed to the polymerization. A useful amount may be from 0.01% to 1% by weight, conveniently 0.05 to 0.5% by weight, alternatively 0.01 to 0.3% by weight or from 0.05% to 0.25% by weight. The sulfinate-containing molecules can be added at the start of the polymerization and/or may be added during the polymerization in a continuous way and/or portion-wise. Preferably, the sulfinate-containing molecule is continuously fed to the polymerization.

The polymers can be obtained with any of the known polymerization techniques including solution polymerization, suspension polymerization and polymerization in super critical $CO_2$. The polymers are preferably made through an aqueous emulsion polymerization process, which can be conducted in a known manner including batch, semi-batch, or continuous polymerization techniques. The reactor vessel for use in the aqueous emulsion polymerization process is typically a pressurizable vessel capable of withstanding the internal pressures during the polymerization reaction. Typically, the reaction vessel will include a mechanical agitator, which will produce thorough mixing of the reactor contents and heat exchange system. Any quantity of the monomer(s) and the sulfinate-containing molecules may be charged to the reactor vessel. The monomers and/or the sulfinate-containing molecules may be charged batchwise or in a continuous or semicontinuous manner. By semi-continuous is meant that a plurality of batches of the monomer and/or and the sulfinate-containing molecules are charged to the vessel during the course of the polymerization. The independent rate at which the monomers and/or the sulfinate-containing molecules are added to the kettle, will depend on the consumption rate with time of the particular monomer and/or the sulfinate-containing molecule. Preferably, the rate of addition of monomer and/or the sulfinate-containing molecules will equal the rate of consumption of monomer, i.e. conversion of monomer into polymer, and/or the sulfinate-containing molecules.

The reaction kettle is charged with water. To the aqueous phase there is generally also added a fluorinated surfactant, typically a non-telogenic fluorinated surfactant although aqueous emulsion polymerization without the addition of fluorinated surfactant may also be practiced. When used, the fluorinated surfactant is typically used in amount of 0.01% by weight to 1% by weight. Suitable fluorinated surfactants include any fluorinated surfactant commonly employed in aqueous emulsion polymerization. Particularly preferred fluorinated surfactants are those that correspond to the general formula:

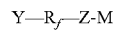

wherein Y represents hydrogen, Cl or F; $R_f$ represents a linear or branched perfluorinated alkylene having 4 to 10 carbon atoms; Z represents $COO^-$ or $SO_3^-$ and M represents an alkali metal ion or an ammonium ion. Exemplary emulsifiers include: ammonium salts of perfluorinated alkanoic acids, such as perfluorooctanoic acid and perfluorooctane sulphonic acid.

Also contemplated for use in the preparation of the polymers described herein are emulsifiers of the general formula:

wherein L represents a linear partially or fully fluorinated alkylene group or an aliphatic hydrocarbon group, $R_f$ represents a linear partially or fully fluorinated aliphatic group or a linear partially or fully fluorinated group interrupted with one or more oxygen atoms, $X_i^+$ represents a cation having the valence i and i is 1, 2 and 3. Specific examples are described in, for example, US Pat. Publ. 2007/0015937 (Hintzer et al.). Exemplary emulsifiers include: $CF_3CF_2OCF_2CF_2OCF_2COOH$, $CHF_2(CF_2)_5COOH$, $CF_3(CF_2)_6COOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_3(CH_2CF_2)_2CF_2CF_2CF_2COOH$, $CF_3(CF_2)_2CH_2(CF_2)_2COOH$, $CF_3(CF_2)_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, and their salts. In one embodiment, the molecular weight of the emulsifier is less than 1500, 1000, or even 500 grams/mole.

These emulsifiers may be used alone or in combination as a mixture of two or more of them. The amount of the emulsifier is well below the critical micelle concentration, generally within a range of from 250 to 5,000 ppm (parts per million), preferably 250 to 2000 ppm, more preferably 300 to 1000 ppm, based on the mass of water to be used.

A chain transfer agent may be used to control the molecular weight of the polymer so as to obtain the desired zero shear rate viscosity. Useful chain transfer agents include $C_2$-$C_6$ hydrocarbons such as ethane, alcohols, ethers, esters including aliphatic carboxylic acid esters and malonic esters, ketones and halocarbons. Particularly useful chain transfer agents are dialkylethers such as dimethyl ether and methyl tertiary butyl ether.

In one embodiment, the polymerization is initiated after an initial charge of the monomer and/or the sulfinate-containing molecule by adding an initiator or initiator system to the aqueous phase. For example peroxides can be used as free radical initiators. Specific examples of peroxide initiators include, hydrogen peroxide, diacylperoxides such as diacetylperoxide, dipropionylperoxide, dibutyrylperoxide, dibenzoylperoxide, benzoylacetylperoxide, diglutaric acid peroxide and dilaurylperoxide, and further water soluble per-acids and water soluble salts thereof such as e.g. ammonium, sodium or potassium salts. Examples of per-acids include peracetic acid. Esters of the peracid can be used as well and examples thereof include tert-butylperoxyacetate and tert-butylperoxypivalate. A further class of initiators that can be used are water soluble azo-compounds. Suitable redox systems for use as initiators include for example a combination of peroxodisulphate and hydrogen sulphite or disulphite, a combination of thiosulphate and peroxodisulphate or a combination of peroxodisulphate and hydrazine. Exemplary persulphates include: sodium peroxodisulphates, potassium peroxodisulphates, ammonium peroxodisulphates.

In yet another embodiment, a second fluoroalkyl sulfinates can be used in conjection with oxidizing agents to initiate the polymerization. Exemplary second fluoroalkyl sulfinates include: $C_4F_9SO_2M$, wherein M is a cation. Further initiators that can be used are ammonium-alkali- or earth alkali salts of persulfates, permanganic or manganic acid or manganic acids. The amount of initiator employed is typically between 0.03 and 2% by weight, preferably between 0.05 and 1% by weight based on the total weight of the polymerization mixture. The full amount of initiator may be added at the start of the polymerization or the initiator can be added to the polymerization in a continuous way during the polymerization until a conversion of 70 to 80%. One can also add part of the initiator at the start and the remainder in one or separate additional portions during the polymerization. Accelerators such as for example water-soluble salts of iron, copper and silver may also be added.

During the initiation of the polymerization reaction, the sealed reactor kettle and its contents are conveniently preheated to the reaction temperature. Polymerization temperatures are from 20° C. to 150° C., preferred from 30° C. to 110° C. and most preferred from 40° C. to 100° C. The polymerization pressure is typically between 4 and 30 bar, in particular 8 to 20 bar. The aqueous emulsion polymerization system may further comprise auxiliaries, such as buffers and complex-formers.

The amount of polymer solids that can be obtained at the end of the polymerization is typically between 10% and 45% by weight, preferably between 20% and 40% by weight and the average particle size of the resulting fluoropolymer is typically between 50 nm and 500 nm.

In one embodiment, a polymer comprising an end-group according to formulas III and IV may be obtained, wherein the end-group has a structures of:

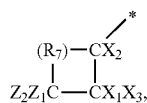

Formula (III)

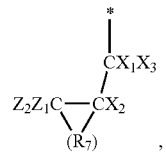

Formula (IV)

and combinations thereof;

wherein $X_1$, $X_2$, and $X_3$ are each independently selected from H, F, Cl, a $C_1$ to $C_4$ alkyl group, and a $C_1$ to $C_4$ fluorinated alkyl group; and $Z_1$ and $Z_2$ are independently selected from F, $CF_3$, and a perfluoroalkyl group. $R_7$ is a linking group that can be a linear or branched, cyclic or acyclic structure, that may be saturated or unsaturated, substituted or unsubstituted, and optionally contains one or more hetero-atoms selected from the group consisting of sulfur, oxygen, and nitrogen, and/or optionally contains one or more functional groups selected from the group consisting of ester, amide, sulfonamide, carbonyl, carbonate, urethane, urea, and carbamate. $R_7$ comprises at least 2 or more catenary atoms so that at a minimum a 5-membered ring is achieved. As used herein the asterisk (*) is used to designate a polymer chain.

In one embodiment, these end-groups of Formula (III) and/or (IV) can originated from the intramolecular cyclization of the sulfinate-containing molecule, for example the vinyl sulfinated monomers of Formula (I).

Exemplary endgroups include:

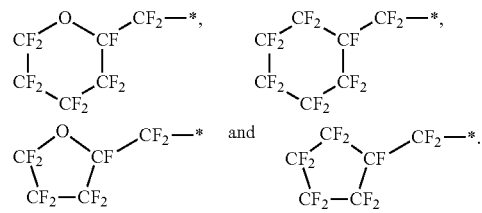

However, other end-groups derived from the sulfinate-containing molecule may be contemplated.

In one embodiment, the polymer comprising an end-group according to formulas III and IV may further comprise interpolymerized units of a monomer. Such monomers may be selected from: dienes (including nonfluorianted, partially fluorinated and perfluorinated dienes, for example $CH_2=CHR_fCH=CH_2$, wherein Rf is a perfluorinated alkylene group, which may comprise 2, 3, 4, 5, 6, 7, 8, 9, 10, 11, 12 carbon atoms for example), halogenated alkenes, a fluoroalkyl substituted ethylene, allyl iodide, fluorinated alkyl vinyl ethers, fluorinated alkoxy vinyl ethers, olefins, acrylates, styrene, vinyl ethers, and combinations thereof.

Exemplary monomers include: tetrafluoroethylene, hexafluoropropylene, trifluoroethylene, vinylidene fluoride, vinyl fluoride, bromotrifluoroethylene, chlorotrifluoroethylene, $CF_3CH=CF_2$, $C_4F_9CH=CH_2$, $CF_2=CHBr$, $CH_2=CHCH_2Br$, $CF_2=CFCF_2Br$, $CH_2=CHCF_2CF_2Br$, $CH_2=CH_1$, $CF_2=CHI$, $CF_2=CF_1$, $CH_2=CHCH_2I$, $CF_2=CFCF_2I$, $CH_2=CHCF_2CF_2I$, $CF_2=CFCH_2CH_2I$, $CF_2=CFCF_2CF_2I$, $CH_2=CH(CF_2)_6CH_2CH_2I$, $CF_2=CFOCF_2CF_2I$, $CF_2=CFOCF_2CF_2CF_2I$, $CF_2=CFOCF_2CF_2CH_2I$, $CF_2=CFCF_2OCH_2CH_2I$, $CF2=CFO(CF2)3-OCF2CF2$, $CH2=CHBr$, and others as is known in the art.

The fluorine-containing polymer of the present disclosure may be used as a gasket, a seal, a film, or a hose.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, hr=hour, kg=kilograms, min=minutes, cm=centimeter, mm=millimeter, ml=milliliter, dl=deciliter, l=liter, mol=moles, kPa=kilopascals, MPa=megapascals, FT-IR=Fouier Transform Infrared Spectroscopy, psig=pounds per square inch gauge, [η]=intrinsic viscosity, rad/s=radians/sec SI unit of angular velocity, MV=Mooney Viscosity, MI=melt index in g/10 min @ 190° C. and 2.6 kg weight, and wt=weight, LCBI=Long Chain Branching Index.

Methods

Mooney Viscosity

Mooney viscosity was determined in accordance with ASTM D1646-06 Part A by a MV 2000 instrument (available from Alpha Technologies, Akron, Ohio) using large rotor (ML 1+10) at 121° C. Results are reported in Mooney units.

Melt Flow Index:

The melt flow index (MFI), reported in g/10 min, was measured at a temperature of 265° C. according to DIN EN ISO 1133 with a support weight of 5.0 kg. The MFI was obtained with a standardized extrusion die of 2.095 mm diameter and a length of 8.0 mm.

Melting Point:

Melting peaks of the fluororesins were determined according to ASTM 4591 by means of Perkin-Elmer DSC 7.0 under nitrogen flow and a heating rate of 10° C./min. The indicated melting points relate to the melting peak maximum.

Characterization of the Shear Melt Rheology:

Oscillatory shear flow measurements were conducted on fluoropolymer melts using a strain controlled ARES rheometer (Advanced Rheological Expansion System; 3ARES-13; Firmware version 4.04.00) of Rheometric Scientific/TA Instruments (Alzenau, Germany) equipped with a 2KFRT 200 force rebalance transducer (supplied by RheoService, Reichelsheim, Germany) with a force range of up to 200 g. Dynamic mechanical data were recorded in nitrogen atmosphere in frequency sweep experiments using a 25 mm parallel plate geometry and a temperature of 265° C. The thermal control of the oven was operated using the sample/tool thermal element. Zero shear viscosities $\eta_0$, reported in Pa·s, were extracted from stress relaxation experiments conducted with 12% strain. The zero shear viscosity was obtained by the stress relaxation integration procedure provided by the "Transforms" function of the orchestrator software.

Particle Size Determination:

The latex particle size determination was conducted by means of dynamic light scattering with a Malvern Zetasizer 1000 HSA in accordance to ISO/DIS 13321. The reported average particle size is the z-average. Prior to the measurements, the polymer latexes as yielded from the polymerizations were diluted with 0.001 mol/L KCl-solution, the measurement temperature was 20° C. in all cases.

Solution Viscosities:

Solution viscosities of diluted polymer solutions were determined on a 0.16% polymer solution in methylethylketone (MEK) at 35° C. in accordance to DIN EN ISO 1628-1. A Connon-Fenske-Routine-Viskosimeter (Fa. Schott, Mainz/Germany) fulfilling ISO/DIS 3105 and ASTM D 2515 was used for the measurements, the Hagenbach correction was applied. The so-obtained reduced viscosities $\eta_{red.}$ were converted into the intrinsic viscosity [η] using the Huggins equation ($\eta_{red.}=[\eta]+k_H \times [\eta]^2 \times c$) and a Huggins constant of $k_H=0.34$. The long chain branching index LCBI was evaluated as described herein and by the following equation (referenced in U.S. Pat. No. 7,375,157) using the [η] from solution viscosity and the $\eta_0$ from melt rheology investigation.

The values a and k along with the test conditions for some of the fluoropolymers that may be used in the melt-processible polymer composition are set forth in the following table. U.S. Pat. No. 7,375,157 further describes the derivation of parameters "k" and "a".

| Polymer | test condition | a-value | k-value |
|---|---|---|---|
| $TFE_{39}/HFP_{11}/VDF_{50}$ | A | 5.3 | $2.5 \times 10^{-7}$ |
| $TFE_{24.5}/HFP_{23}/VDF_{52.5}$ | A | 5.3 | $3.8 \times 10^{-7}$ |
| $VDF_{78}/HFP_{22}$ | A | 5.3 | $1.3 \times 10^{-7}$ |
| polyvinylidene fluoride | B | 5.3 | $1.2 \times 10^{-7}$ |
| polyvinylidene fluoride | C | 5.3 | $2.2 \times 10^{-7}$ |

In the above table, the indexes to the monomer units in the polymer indicate the amount of the respective unit in mole % and the test conditions are as follows:

A: shear viscosity at 265° C. and the intrinsic viscosity in methyl ethyl ketone at 35° C.

B: shear viscosity at 230° C. and the intrinsic viscosity in dimethylformamide at 23° C.

C: shear viscosity at 230° C. and the intrinsic viscosity in dimethylformamide at 110° C.

It can be observed from the above table that the constant a appears to be independent of the fluoropolymer tested whereas the k-value varies with composition of the fluoropolymer and test condition used.

MV4SO2H and MV4SO2NH4 Synthesis 50 g (0.13 mol) MV4S and 150 ml of reagent grade ethanol were added to a 1 liter 3-neck round bottom flask. The solution was stirred and cooled to 0° C. 3.4 g (0.09 mol) $NaBH_4$ was added in portions over 30 minutes with a 5° C. exothermic temperature rise per portion. The reaction was kept under 10° C. throughout the addition of $NaBH_4$. The flask was allowed to warm to 20° C. and the slurry was stirred for 30 minutes. 26 g concentrated $H_2SO_4$ in 200 g water was added slowly resulting in a temperature rise to 32° C. A lower fluorochemical phase of 31 g of unreacted MV4S was recovered. The clear top solution was extracted with 110 g methyl-t-butyl ether (MTBE) and vacuum stripped to recover 28 g of a semi-solid material. The semi-solid material still contained some water, ethanol, and salts. NMR gave the desired MV4SO2H in an 86% yield based on reacted MV4S. The ammonium salt MV4SO2NH4 was made by titration with ammonium hydroxide.

Synthesis of $CH_2=CH(CF_2)_3SO_2H$

In a 600 mL PARR pressure reactor, 198.4 g (MW=404, 0.491 mol) $I(CF_2)_3I$ was reacted with 15.4 g (MW=28, 0.55 mol) $CH_2\!=\!CH_2$ (charged in portions) in the presence of 4.58 g "VAZO-67" (E.I. du Pont de Nemours & Co, Wilmington, Del.) at 60° C. for 24 hrs under 60 psig (414 kPa) or less. Distillation afforded 95 g $ICH_2CH_2CF_2CF_2CF_2I$ with a boiling point at 54-62° C. at 1 mm-Hg. From $^{19}F$ NMR analysis, the NMR purity is ~98% with small amount of unreacted $I(CF_2)_3I$ and bis-adduct, $I(CH2)2(CF2)3(CH2)2I$ (isolated yield: ~44.8%). $^{19}F$ NMR analysis confirmed the product: −58 ppm (txt, 2F, —CF2I), −113 (txt, 2F), −114 (m, 2F); $^1H$ NMR of $ICH_2CH_2CF_2CF_2CF_2I$: 3.5 ppm (m, 2H), 3.0 (m, 2H, —CF2CH2-).

Under nitrogen, 43.5 g (MW=432, 0.1 mol) of the above distilled $ICH_2CH_2CF_2CF_2CF_2I$ was treated with 26 g $Na_2S_2O_4$ (MW=174, 91%, 0.136 mol) and 13 g $NaHCO_3$ (MW=84, 0.154 mol) in 50 g $CH_3CN$ and 68 g $H_2O$ at room temperature for 2 hrs. $^{19}F$ NMR analysis of the reaction solution showed complete conversion of —$CF_2I$ (−67 ppm) to form the corresponding —$CF_2SO_2Na$ at ~−130 ppm yielding the desired $ICH_2CH_2(CF_2)_3SO_2Na$. The mixture was filtered to remove solids. The filtered solution showed two phases, and only top phase showed fluorinated product based on $^{19}F$ NMR analysis. The top phase was separated, and the solvents were removed by rotary evaporation to give 48 g wet solid. The wet solid was dissolved in water and the following chemical shifts were recorded and confirmed the designed product. $^{19}F$ NMR of $ICH_2CH_2CF_2CF_2CF_2SO_2Na$: −115 ppm (dxtxt, 2F, —CF2CH2-), −124 (m, 2F), −130 (t, 2F, —CF2SO2M); $^1H$ NMR of $ICH_2CH_2CF_2CF_2CF_2SO_2Na$: 3.2 ppm (txm, 2H, —CF2CH2-), 2.5-3.0 (m, 2H, —CH2I).

The above $ICH_2CH_2(CF_2)_3SO_2Na$ wet solid was dissolved in ethanol and treated with 8.7 g KOH (MW=56, 85%, 0.132 mol) at room temperature, then the mixture was reacted at 50° C. for 8 hrs to precipitate a solid (KI). The reaction mixture was cooled to 20° C. and filtered to remove solids. No significant change in $^{19}F$ NMR was observed. The solvent was stripped and the resulting solid was acidified with $2NH_2SO_4$ to a pH<2. The acidified solution was extracted with t-butylmethyl ether (three times, 100 mL each) and the combined ether solution was dried over $MgSO_4$. Finally, the solution was filtered and the solvent was stripped to yield 21.5 g (MW=242, 88.8 mmol) desired semisolid product, $CH_2\!=\!CH(CF_2)_3SO_2H$, which is soluble in water. The structure of the product was confirmed by NMR analyses, $^{19}F$ NMR, −115 (dxt, 2F, =CHCF2-), −125 (txm, 2F), −127 (t, 2F, —CF2SO2H). $^1H$ NMR, 4.4~5.6 (m) ppm, indicating no more $ICH_2CH_2$— signal. The isolated yield is ~88.8% from $ICH_2CH_2CF_2CF_2CF_2I$.

Synthesis of MV4SO2NH4

Oligomerization of CF2=CF—O—C4F8-SO2F (MV4S) was done in a 600 ml PARR reactor by charging 200 g MV4S and 20 g LUPEROX 575 and reacting for 20 hours at 65° C. Vacuum distillation removed the lower boiling cut and the product remaining in the pot had a boiling point greater than 220° C. at 5 mm vacuum. Reduction of 25 g of oligomeric MV4S (o-MV4S) with 6 g NaBH4 in 100 g tetrahydrofuran (THF) was done for one hour at 65° C. The mixture was cooled down and 14 g of concentrated sulfuric acid in 200 g water was added. The product top phase was vacuum stripped to remove solvent and the product was dissolved in 50 g methanol, filtered and vacuum stripped to yield 25 g of oligomeric multisulfinic acid (o-MV4SO2H) which was made into a 50% aqueous solution. A 5 g sample was neutralized with 27% ammonium hydroxide and vacuum dried to a solid yielding the fluoro oligomeric multisulfinic acid ammonium salt (o-MV4SO2NH4).

| Materials | |
|---|---|
| Material Name | Description |
| MV4S | $CF_2\!=\!CF$—O—$C_4F_8$—$SO_2F$, made as described in the Example (section A to C) of U.S. Pat. No. 6,624,328 (Guerra) |
| MV4SO2H/MV4SO2NH4 | $CF_2\!=\!CFOC_4F_8SO_2H$ and ammonium salt synthesized as per "MV4SO2H AND MV4SO2NH4 SYNTHESIS" |
| $I(CF_2)_3I$ | May be obtained by distillation purification from the reaction mixture of U.S. Pat. No. 6,002,055 Example 6. |
| $CF_3OCF_2CF_2CF_2OCF_2CO_2$—$NH_4+$ | Emulsifier prepared as per "Preparation of Compound 1" in U.S. Pat. No. 7,754,795. |
| o-MV4SO2NH4 | R—$[CF_2CF(OC_4F_8SO_2NH_4)]$n-R where n = 2-5 and R can be $C_4F_9$, I, H, $C_2H_5$ and/or $C_7H_{15}$ as per "MV4SO2NH4 SYNTHESIS" |

Example 1

A 4 liter reactor was charged with 2,250 g water, 1.7 g of diethyl malonate (DEM), an aqueous solution containing 5.2 g ammonium persulfate (APS, $(NH_4)_2S_2O_8$), and 5.0 g potassium phosphate dibasic ($K_2HPO_4$). Containers from which the solid reagents were added were rinsed, and the rinse water, totaling 350 g, was added to the reactor. The reactor was evacuated; the vacuum was broken and the vessel was pressurized with nitrogen to 25 psig (0.17 MPa). This evacuation and pressurization cycle was repeated three times. After removing oxygen, the reactor was heated to 73.3° C. and pressurized with 22 g hexafluoropropylene (HFP). The reactor was then charged with 139 g vinylidene fluoride (VDF) and 109 g hexafluoropropylene (HFP). The reactor was agitated at 650 rpm. As reactor pressure dropped due to monomer consumption in the polymerization reaction, HFP and VDF were continuously fed to the reactor to maintain the pressure at 160 psig (1.11 MPa). The ratio of HFP and VDF was 0.651 by weight. Concurrently, a 20% w/w solution of MV4SO2NH4 vinyl sulfinate monomer was fed continuously, such that 15 g monomer (75 g solution) was fed over the course of the polymerization. After 750 g VDF had been introduced, the monomer feeds were discontinued and the reactor was cooled. The resulting dispersion had a solid content of 31.1 wt % and a pH of 3.4. The mean particle size in the latex was 259 nm and the total amount of dispersion was about 3,880 g.

For the coagulation, 3000 g of the dispersion made as described above was added to 3038 g of a 1.25 wt % aqueous solution of $MgCl_2$. The crumb was recovered by filtering the coagulate through cheese cloth and gently squeezing to remove excess water. The crumb was returned to the coagulation vessel and rinsed with deionized water a total of 4 times. After the final rinse and filtration, the crumb was dried in a 130° C. oven for 16 hrs. The resulting fluoroelastomer raw gum had a Mooney viscosity of 55 at 121° C.

The fluoroelastomer by FT-IR analysis contained 79.7 mol % copolymerized units of VDF and 20.3 mol % HFP. The fluorine content was 65.6 wt %.

Examples 2-7

Polymerizations were carried out as in Example 1, except that the amount of MV4SO2NH4 vinyl sulfinate monomer introduced during the course of the polymerizations was reduced to 10 g and the reaction temperatures and pressures were varied as indicated in Table 1.

Examples 8-10

Polymerizations were carried out as in Example 1, with the exception that the MV4SO2NH4 vinyl sulfinate monomer was replaced with a partially fluorinated non ether vinyl sulfinate monomer, $CH_2=CH(CF_2)_3SO_2H$ (monomer made as described under "$CH_2=CH(CF_2)_3SO_2H$ Synthesis"). The reaction pressures were varied as indicated in Table 1.

Comparative Example 1

A polymerization was carried out as in Example 1, with the exception that there was no vinyl sulfinate monomer in the recipe. See Table 1.

Example 11

A 4 l reactor was charged with 2,250 g water, 1.8 g diethyl malonate (DEM), and an aqueous solution containing 9.7 g ammonium persulfate (APS, $(NH_4)_2S_2O_8$), 5.3 g potassium phosphate dibasic ($K_2HPO_4$), and 5.0 g MV4SO2NH4 vinyl sulfinate monomer in 100 g water. Containers from which the solid reagents were added were rinsed, and the rinse water, totaling 325 g, was added to the reactor. The reactor was then evacuated; after the vacuum was broken, the vessel was pressurized with nitrogen to 25 psig (0.17 MPa). This evacuation and pressurization cycle was repeated three times. After removing oxygen, the reactor was heated to 71.1° C. and pressurized to 40 psig (0.27 MPa) with hexafluoropropylene (HFP). The reactor was then charged with a mixture of vinylidene fluoride (VDF), hexafluoropropylene (HFP), and tetrafluoroethylene (TFE) to reach the polymerization condition of 160 psig (1.11 MPa) within the reactor. The ratio of HFP to VDF in the pressure-up was 3.24 by weight, and the ratio of TFE to VDF in the pressure-up was 1.00. The reactor was agitated at 650 rpm. As reactor pressure dropped due to monomer consumption in the polymerization reaction, HFP, VDF, and TFE were continuously fed to the reactor to maintain the pressure at 160 psig (1.11 MPa). The ratio of HFP and VDF was maintained at 1.24 by weight, while the ratio of TFE and VDF was maintained at 0.73. After 425 grams of VDF had been introduced, the monomer feeds were discontinued and the reactor was cooled. The resulting dispersion had a solid content of 33.1 wt % and a pH of 2.8. The mean particle size in the latex was 63 nm and the total amount of dispersion was about 4,010 grams.

For the coagulation, 3000 g of the dispersion made as described above was added to 3038 g of a 1.25 wt % aqueous solution of $MgCl_2$. The crumb was recovered by filtering the coagulate through cheese cloth and gently squeezing to remove excess water. The crumb was returned to the coagulation vessel and rinsed with deionized water a total of 4 times. After the final rinse and filtration, the crumb was dried in a 130° C. oven for 16 hrs. The resulting fluoroelastomer raw gum had a Mooney viscosity of 83 at 121° C.

The fluoroelastomer by FT-IR analysis contained 53.2 mol % copolymerized units of VDF, 19.5 mol % TFE, and 27.3 mol % HFP. The fluorine content was 70.0 wt %.

Example 12

A 4 liter reactor was charged with 2,250 g water, 1.8 g diethyl malonate (DEM), an aqueous solution containing 9.7 g ammonium persulfate (APS, $(NH_4)_2S_2O_8$), and 5.3 g of potassium phosphate dibasic ($K_2HPO_4$). Containers from which the solid reagents were added were rinsed, and the rinse water, totaling 375 g, was added to the reactor. The reactor was then evacuated; after the vacuum was broken, the vessel was pressurized with nitrogen to 25 psig (0.17 MPa). This evacuation and pressurization cycle was repeated three times. After removing oxygen, the reactor was heated to 71.1° C. and pressurized to 40 psig (0.27 MPa) with hexafluoropropylene (HFP). The reactor was then charged with a mixture of vinylidene fluoride (VDF), hexafluoropropylene (HFP), and tetrafluoroethylene (TFE) to reach the polymerization condition of 160 psig (1.11 MPa) within the reactor. The ratio of HFP to VDF in the pressure-up was 3.24 by weight, and the ratio of TFE to VDF in the pressure-up was 1.00. The reactor was agitated at 650 rpm. As reactor pressure dropped due to monomer consumption in the polymerization reaction, HFP, VDF, and TFE were continuously fed to the reactor to maintain the pressure at 160 psig (1.11 MPa). The ratio of HFP and VDF was maintained at 1.24 by weight, while the ratio of TFE and VDF was maintained at 0.73. Concurrently, a 10% w/w solution of MV4SO2NH4 vinyl sulfinate monomer was fed continuously, such that 5 g monomer (50 g solution) was fed over the course of the polymerization. After 425 g VDF had been introduced, the monomer feeds were discontinued and the reactor was cooled. The resulting dispersion had a solid content of 33.2 wt % and a pH of 2.6. The mean particle size in the latex was 307 nm and the total amount of dispersion was about 3,900 g.

For the coagulation, 3000 g of the dispersion made as described above was added to 3038 g of a 1.25 wt % aqueous solution of $MgCl_2$. The crumb was recovered by filtering the coagulate through cheese cloth and gently squeezing to remove excess water. The crumb was returned to the coagulation vessel and rinsed with deionized a total of 4 times. After the final rinse and filtration, the crumb was dried in a 130° C. oven for 16 hrs. The resulting fluoroelastomer raw gum had a Mooney viscosity of 96 at 121° C.

The fluoroelastomer by FT-IR analysis contained 52.1 mol % copolymerized units of VDF, 20.8 mol % TFE, and 27.1 mol % HFP. The fluorine content was 70.1 wt %.

Examples 13-15

Polymerizations were carried out as in Example 12, except that the amount of vinyl sulfinate monomer was varied as indicated in Table 1.

Comparative Example 2

A polymerization was carried out as in Example 11, with the exception that there was no vinyl sulfinate monomer in the recipe. See Table 1.

Example 16

A 4 l reactor was charged with 2,250 g water, 1.5 g diethyl malonate (DEM), 1.0 g o-MV4SO2NH4, and an aqueous solution containing 6.0 g ammonium persulfate (APS, $(NH_4)_2S_2O_8$) and 5.0 g MV4SO2NH4 vinyl sulfinate monomer in 50 g water. Containers from which the solid reagents were added were rinsed, and the rinse water, totaling 375 g, was added to the reactor. The reactor was then evacuated; after the vacuum was broken, the vessel was pressurized with nitrogen to 25 psig (0.17 MPa). This evacuation and pressurization cycle was repeated three times. After removing oxygen, the reactor was heated to 80° C. and the vacuum was broken by adding 22 grams of hexafluoropropylene (HFP). The reactor was then charged with a mixture of vinylidene fluoride (VDF), hexafluoropropylene (HFP), and tetrafluoroethylene (TFE) to reach the polymerization condition of 160 psig (1.11 MPa) within the reactor. The ratio of HFP to VDF in the pressure-up was 5.4 by weight, and the ratio of TFE to VDF in the pressure-up was 2.7. The reactor was agitated at 650 rpm. As reactor pressure dropped due to monomer consumption in the polymerization reaction, HFP, VDF, and TFE were continuously fed to the reactor to maintain the pressure at 160 psig (1.11 MPa). The ratio of HFP and VDF was maintained at 0.63 by weight, while the ratio of TFE and VDF was maintained at 1.83. After 232 grams of VDF had been introduced, the monomer feeds were discontinued and the reactor was cooled. The resulting dispersion had a solid content of 21.0 wt % and a pH of 2.0. The mean particle size in the latex was 115 nm and the total amount of dispersion was about 3,340 grams.

For the coagulation, 3000 g of the dispersion made as described above was added to 3038 g of a 1.25 wt % aqueous solution of $MgCl_2$. The crumb was recovered by filtering the coagulate through cheese cloth and gently squeezing to remove excess water. The crumb was returned to the coagulation vessel and rinsed with deionized water a total of 4 times. After the final rinse and filtration, the crumb was dried in a 105° C. oven for 16 hrs.

Example 17

A 4 l reactor was charged with 2,250 g water, 1.5 g diethyl malonate (DEM), 1.0 g o-MV4SO2NH4 and an aqueous solution containing 6.0 g ammonium persulfate (APS, $(NH_4)_2S_2O_8$) in 50 g water. Containers from which the solid reagents were added were rinsed, and the rinse water, totaling 325 g, was added to the reactor. The reactor was then evacuated; after the vacuum was broken, the vessel was pressurized with nitrogen to 25 psig (0.17 MPa). This evacuation and pressurization cycle was repeated three times. After removing oxygen, the reactor was heated to 80° C. and pressurized the vacuum was broken by adding 22 g hexafluoropropylene (HFP). The reactor was then charged with a mixture of vinylidene fluoride (VDF), hexafluoropropylene (HFP), and tetrafluoroethylene (TFE) to reach the polymerization condition of 160 psig (1.11 MPa) within the reactor. The ratio of HFP to VDF in the pressure-up was 5.4 by weight, and the ratio of TFE to VDF in the pressure-up was 2.7. The reactor was agitated at 650 rpm. As reactor pressure dropped due to monomer consumption in the polymerization reaction, HFP, VDF, and TFE were continuously fed to the reactor to maintain the pressure at 160 psig (1.11 MPa). The ratio of HFP and VDF was maintained at 0.63 by weight, while the ratio of TFE and VDF was maintained at 1.83. Concurrently, a 10% w/w solution of MV4SO2NH4 vinyl sulfinate monomer was fed continuously, such that 5 g monomer (50 g solution) was fed over the course of the polymerization. After 232 g VDF had been introduced, the monomer feeds were discontinued and the reactor was cooled. The resulting dispersion had a solid content of 15.3 wt % and a pH of 2.0. The mean particle size in the latex was 105 nm and the total amount of dispersion was about 3,091 g.

For the coagulation, 3000 g of the dispersion made as described above was added to 3038 g of a 1.25 wt % aqueous solution of $MgCl_2$. The crumb was recovered by filtering the coagulate through cheese cloth and gently squeezing to remove excess water. The crumb was returned to the coagulation vessel and rinsed with deionized water a total of 4 times. After the final rinse and filtration, the crumb was dried in a 105° C. oven for 16 hrs.

Examples 18-19

Polymerizations were carried out as in Example 17, except that the amount of MV4SO2NH4 vinyl sulfinate monomer was varied as indicated in Table 1.

Comparative Example 3

A polymerization was carried out as in Example 16, with the exception that there was no vinyl sulfinate monomer in the recipe. See Table 1.

TABLE 1

| Example | Vinyl sulfinate monomer (g) | Polymer and Polymerization type Batch (B) Continuous C) | Temp (° C.) | Press (psig) | Rxn time (min) | Solids (%) | Mooney viscosity |
|---|---|---|---|---|---|---|---|
| EX1 | [1]VM1 (15) | Dipolymer (C) | 73.3 | 160 | 182 | 31.1 | 55 |
| EX2 | VM1 (10) | Dipolymer (C) | 73.3 | 160 | 175 | 30.8 | 61 |
| EX3 | VM1 (10) | Dipolymer (C) | 61.7 | 160 | 286 | 29.7 | 88 |
| EX4 | VM1 (10) | Dipolymer (C) | 50.0 | 160 | 496 | 20.6 | 99 |
| EX5 | VM1 (10) | Dipolymer (C) | 73.3 | 130 | 229 | 30.5 | 51 |
| EX6 | VM1 (10) | Dipolymer (C) | 80.0 | 130 | 270 | 31.0 | 48 |
| EX7 | VM1 (10) | Dipolymer (C) | 61.7 | 130 | 378 | 31.2 | 66 |
| CE1 | (0) | Dipolymer | 73.3 | 160 | 170 | 30.3 | 88 |
| EX8 | [2]VM2 (10) | Dipolymer (C) | 80.0 | 130 | 370 | 19.1 | 36 |
| EX9 | VM2 (10 | Dipolymer (C) | 80.0 | 160 | 283 | 24.0 | 50 |

TABLE 1-continued

| Example | Vinyl sulfinate monomer (g) | Polymer and Polymerization type Batch (B) Continuous C) | Temp (° C.) | Press (psig) | Rxn time (min) | Solids (%) | Mooney viscosity |
|---|---|---|---|---|---|---|---|
| EX10 | VM2 (10) | Dipolymer (C) | 80.0 | 190 | 247 | 30.3 | 63 |
| EX11 | VM1 (5) | Terpolymer (B) | 71.1 | 160 | 164 | 33.1 | 83 |
| EX12 | VM1 (5) | Terpolymer (C) | 71.1 | 160 | 156 | 33.2 | 96 |
| EX13 | VM1 (10) | Terpolymer (C) | 71.1 | 160 | 138 | 34.3 | 76 |
| EX14 | VM1 (15) | Terpolymer (C) | 71.1 | 160 | 151 | 33.9 | 60 |
| EX15 | VM1 (20) | Terpolymer (C) | 71.1 | 160 | 160 | 32.8 | 41 |
| CE2 | (0) | Terpolymer | 71.1 | 160 | 189 | 32.4 | 85 |
| EX16 | VM1 (5) | THV (B) | 80.0 | 160 | 342 | 21.0 | NA |
| EX17 | VM1 (5) | THV (C) | 80.0 | 160 | 260 | 15.3 | NA |
| EX18 | VM1 (10) | THV (C) | 80.0 | 160 | 197 | 13.2 | NA |
| EX19 | VM1 (15) | THV (C) | 80.0 | 160 | 170 | 11.3 | NA |
| CE3 | (0) | THV | 80.0 | 160 | 360 | 21.2 | NA |

[1]VM1 = MV4SO2NH4
[2]VM2 = CH2=CH (CF$_2$)$_3$SO$_2$H
NA = not available

Example 20

A thermoplastic TFE$_{39}$/HFP$_{11}$/VDF$_{50}$ terpolymer was prepared in a pilot plant reactor. Herein, a controlled amount of long-chain branching was introduced into the polymer backbone by employing MV4SO2NH4 salt as branching modifier.

The oxygen free polymerization reactor with a total volume of 48.5 l equipped with an impeller agitator system was charged with 29 l deionized water, 230 g of a 30% solution of emulsifier CF$_3$OCF$_2$CF$_2$CF$_2$OCF$_2$CO$_2$—NH$_4^+$, 2.0 g oxalic acid and 12.0 g ammonium oxalate. The reactor was then heated up to 60° C. The agitation system was set to 240 rpm and the kettle was charged with ethane with a partial pressure of 1.7 bar (0.17 MPa). In the following, 936 g hexafluoropropylene (HFP) was charged to a pressure of 8.6 bar absolute (0.86 MPa), with 264 g vinylidene fluoride (VDF) to 12.9 bar absolute (1.29 MPa) and with 405 g tetrafluoroethylene (TFE) to 16.8 bar absolute (1.68 MPa) reaction pressure.

Then, the polymerization was initiated by the addition of 50 ml of a 0.6% aqueous potassium permanganate solution. This initiator solution was in the following continuously fed as feeding rate of 120 ml per hour. As the reaction starts, the reaction temperature was maintained and the reaction pressure of 16.8 bars absolute (1.68 MPa) was also maintained by the feeding TFE, VDF and HFP into the gas phase with a feeding ratio VDF (kg)/TFE (kg) of 0.8204 and HFP (kg)/TFE (kg) of 0.4231. The branching modifier MV4SO2NH4 salt was present in a 30% aqueous solution, which was also fed into the reactor with a feeding ratio of modifier (kg)/TFE (kg) of 0.0673. When a total feed of 6584 g TFE was reached in 216 min, the feed of the monomers was interrupted by closing the monomer valves. Within 10 min, the monomer gas phase was reacted down to a kettle pressure of 12.3 bars. Then the reactor was vented and flushed with nitrogen in three cycles.

The so-obtained 43.7 kg polymer dispersion with a solid content of 34.4% was recovered at the bottom of the reactor. It consisted of latex particles having 105 nm in diameter according to dynamic light scattering and coagulum was discernibly not formed within the polymerizations.

1.01 of this polymer dispersion was freeze coagulated over night in a freezer. After defrosting the material, the so-obtained sponge-like raw polymer was washed five times with demineralised water, the polymer was filtered from the water dried for 36 h in an oven at 90° C. The white polymer powder had the physical characteristics as listed below:

| | |
|---|---|
| MFI (265/5) | 9.1 g/10 min |
| Melting point [° C.] | 119 (1$^{st}$ heat-up)/ 120 (2$^{nd}$ heat-up) |
| Zero shear viscosity at 265° C. | 2.3e4 Pa*s |
| Reduced viscosity (MEK @ 35° C.) | 65 ml/g |
| Intrinsic viscosity (MEK @ 35° C.) | 63 ml/g |
| LCBI | 0.93 |

Linear comparatives for TFE$_{39}$/HFP$_{11}$/VDF$_{50}$ terpolymers prepared in the absence of MV4SO2NH4 salt are described by Auhl et al. in Macromolecules, Vol. 39, No. 6, 2006 and Stange et al. in Macromolecules, Vol. 40, No. 7, 2007.

Example 21

The branched fluoroelastomer of Example 1 was subjected to one-dimensional (1D) and two dimensional (2D) $^1$H-NMR and $^{19}$F-NMR cross integration spectral analyses to determine the fluoroelastomer composition and to characterize the various end group and pendent group sub-structural units. Special emphasis was placed on attempting to detect and quantify any fluoroelastomer sub-structural groups that might be associated with the MV4SO2NH4 co-monomer starting material.

5 mg of the branched fluoroelastomer of Example 1 was totally dissolved in 0.7-0.8 mL of deuterated acetone (acetone-d$_6$) and then the solution was spiked with small amounts of 1,4-bis(trifluoromethyl)benzene (p-HFX), deuterated acetic acid (CD$_3$CO$_2$D), and CFCl$_3$ for NMR analyses. Initial 1D 400 MHz $^1$H-NMR and 376.3 MHz $^{19}$F-NMR spectra were acquired using a Varian VNMRS 400 FT-NMR spectrometer that was operating with a 5 mm inverse-detection gradient probe at a temperature of about 22-23° C. The p-HFX was added to the sample solution for use as a $^1$H/$^{19}$F-NMR cross integration standard to permit the cross correlation of the relative $^1$H and $^{19}$F signal intensities for quantitative purposes. The deuterated acetic acid was added to the sample solution to shift any interfering water proton signal downfield in the $^1$H-NMR spectrum and prevent it from interfering with the fluoroelastomer $^1$H signals of interest. The CFCl$_3$ was added as the $^{19}$F-NMR chemical shift zero calibration reference standard.

The sample solution described above was also used for the acquisition of a 2D $^{19}F/^{19}F$-NMR homonuclear correlated spectroscopy ($^{19}F$-COSY) experiments to permit the observation of $^{19}F/^{19}F$ spin-spin coupling correlations experiments to facilitate assignment of the signals observed in the 1D spectra.

The end group structure

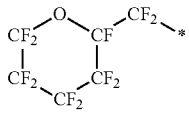

was found present at 0.19% by relative wt %,

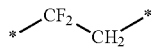

at 61%,

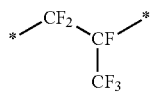

at 38%, R—CF$_2$—H at 0.23%, R—CF$_2$—CH3 at 0.09% and probable

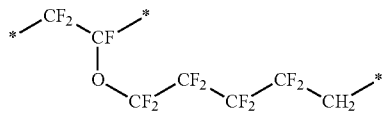

at 0.46%.

Foreseeable modifications and alterations of this invention will be apparent to those skilled in the art without departing from the scope and spirit of this invention. This invention should not be restricted to the embodiments that are set forth in this application for illustrative purposes. To the extent that there is a conflict or discrepancy between this specification and the disclosure in any document incorporated by reference herein, this specification will control.

What is claimed is:

1. A composition comprising:
a fluorine-containing polymer comprising an end-group having a structure selected from:

Formula (III)

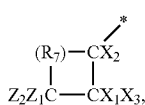

Formula (IV)

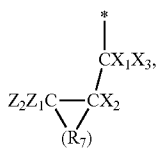

and combinations thereof;

wherein $X_1$, $X_2$, and $X_3$ are each independently selected from H, F, Cl, a $C_1$ to $C_4$ alkyl group, and a $C_1$ to $C_4$ fluorinated alkyl group; $R_7$ is a linking group comprising at least 2 or more catenary atoms; and $Z_1$ and $Z_2$ are independently selected from F, $CF_3$, and a perfluoroalkyl group, wherein the fluorine-containing polymer is partially fluorinated and wherein the fluorine-containing polymer is derived from the polymerization of a monomer and a sulfinate-containing molecule, wherein the sulfinate-containing molecule is selected from the group consisting of:

Formula (I)

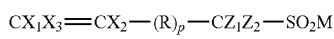

Formula (II)

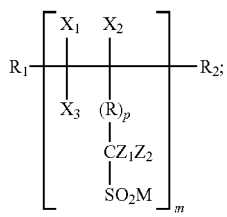

and
(c) combinations thereof,
wherein $X_1$, $X_2$, and $X_3$ are each independently selected from H, F, Cl, a $C_1$ to $C_4$ alkyl group, and a $C_1$ to $C_4$ fluorinated alkyl group; R is a linking group; $Z_1$ and $Z_2$ are independently selected from F, $CF_3$, and a perfluoroalkyl group; $R_1$ and $R_2$ are end-groups; p is 0 or 1; m is at least 2; and M is a cation.

2. The composition of claim 1, wherein the fluorine-containing polymer is crystalline.

3. The composition of claim 1, wherein the fluorine-containing polymer is amorphous.

4. The composition of claim 1, wherein the fluorine-containing polymer has an long chain branching index of greater than 0.2.

5. The composition according to claim 1, wherein the end-group of the fluorine-containing polymer is selected from:

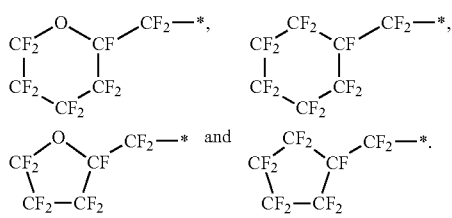

6. The polymer of claim 1, wherein the fluorine-containing polymer comprises interpolymerized units of a monomer, wherein the monomer is selected from: dienes, halogenated alkenes, a fluoroalkyl substituted ethylene, allyl iodide, fluorinated alkyl vinyl ethers, fluorinated alkoxy vinyl ethers, olefins, acrylates, styrene, vinyl ethers, and combinations thereof.

7. The polymer of claim 6, wherein the monomer is selected from: tetrafluoroethylene, hexafluoropropylene, trifluoroethylene, vinylidene fluoride, vinyl fluoride, bromotrifluoroethylene, chlorotrifluoroethylene, $CF_3CH=CF_2$, $C_4F_9CH=CH_2$, $CF_2=CHBr$, $CF_2=CFBr$, $CH_2=CHCH_2Br$, $CF_2=CFCF_2Br$, $CH_2=CHCF_2CF_2Br$, and combinations thereof.

8. The polymer of claim 6, wherein the monomer is vinylidene fluoride.

9. The polymer of claim 6, wherein at least one of $X_1$, $X_2$, and $X_3$ is H.

10. The polymer according to claim 1, wherein the end-group is selected from:

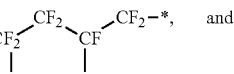
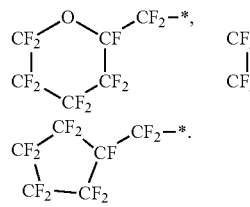
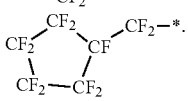

11. The composition according to claim 1, wherein the fluorine-containing polymer is melt-processible.

12. An article comprising the composition of claim 1.

13. The article of claim 12, wherein the article is a gasket, a seal, a film, or a hose.

* * * * *

UNITED STATES PATENT AND TRADEMARK OFFICE
CERTIFICATE OF CORRECTION

PATENT NO. : 10,093,761 B2
APPLICATION NO. : 13/992493
DATED : October 9, 2018
INVENTOR(S) : Gregg Dahlke Page 1 of 1

It is certified that error appears in the above-identified patent and that said Letters Patent is hereby corrected as shown below:

On the Title Page

Column 2,
Line 14, before "$CX_1X_3$" delete "(a)".

In the Specification

Column 4,
Line 36, delete "—O(CF$_2$)—" and insert -- —O(CF$_2$)$_a$— --, therefor.

Column 5,
Line 40, delete "CF2=CFO" and insert -- CF$_2$=CFO --, therefor.
Line 40, delete "OCF2 CF2, CH2=CHBr" and insert -- OCF$_2$CF$_2$, CH$_2$=CHBr --, therefor.
Line 49, delete "SO$_2$." and insert -- SO$_2$· --, therefor.

Column 10,
Line 61, delete "CH$_2$=CH$_1$," and insert -- CH$_2$=CHI, --, therefor.
Line 61, delete "CF$_2$=CF$_1$," and insert -- CF$_2$=CFI, --, therefor.

Column 13,
Line 57, delete "2NH$_2$SO$_4$" and insert -- 2N H$_2$SO$_4$ --, therefor.

Column 15,
Line 40, delete "41 reactor" and insert -- 4 l reactor --, therefor.

Column 17,
Line 9, delete "41 reactor" and insert -- 4 l reactor --, therefor.
Line 50, delete "41 reactor" and insert -- 4 l reactor --, therefor.

Signed and Sealed this
Twelfth Day of February, 2019

Andrei Iancu
*Director of the United States Patent and Trademark Office*